US010532991B2

(12) United States Patent
Huang et al.

(10) Patent No.: US 10,532,991 B2
(45) Date of Patent: Jan. 14, 2020

(54) METHOD FOR PREPARING HISPIDULIN AND ITS DERIVATIVES

(71) Applicant: TAIPEI MEDICAL UNIVERSITY, Taipei (TW)

(72) Inventors: Wei-Jan Huang, Taipei (TW); Kai-Cheng Hsu, Taipei (TW); Lih-Chu Chiou, Taipei (TW); Liang-Chieh Chen, Taipei (TW); Hui-Ju Tseng, Taipei (TW); Pi-Chuan Fan, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 16/177,500

(22) Filed: Nov. 1, 2018

(65) Prior Publication Data
US 2019/0322637 A1    Oct. 24, 2019

Related U.S. Application Data

(60) Provisional application No. 62/659,229, filed on Apr. 18, 2018.

(51) Int. Cl.
C07D 311/30    (2006.01)

(52) U.S. Cl.
CPC ........ *C07D 311/30* (2013.01); *C07B 2200/05* (2013.01)

(58) Field of Classification Search
CPC .................................................. C07D 311/30
USPC ......................................................... 549/403
See application file for complete search history.

(56) References Cited

PUBLICATIONS

Chen, et al. "Total Synthesis and Metabolic Stability of Hispidulin and Its d-Labelled Derivative", Molecules, Nov. 4, 2017.
Pietta, "Flavonoids as antioxidants", J. Nat. Prod. 2000, 63, 1035-1042.
Serafini, et al. "Flavonoids as anti-inflammatory agents", Proc. Nutr. Soc. 2010, 69, 273-278.
Cushnie, et al. "Antimicrobial activity of flavonoids" Int. J. Antimicrob. Agents 2005, 26, 343-356.
Rodriguez, et al. "Anticonvulsant and antioxidant effects of *Tilia americana* var. mexicana and flavonoids constituents in the pentylenetetrazole-induced seizures". Oxid. Med. Cell. Longev. 2014, 2014, 329172.
Guan, et al. "Antidepressant-like effects and mechanisms of flavonoids and related analogues", Eur. J. Med. Chem. 2016, 121, 47-57.
Ravishankar, et al. "Flavonoids as prospective compounds for anti-cancer therapy", Int. J. Biochem. Cell Biol. 2013, 45, 2821-2831.
Fan, et al. "Intractable chronic motor tics dramatically respond to *Clerodendrum inerme* (L) Gaertn", J. Child Neurol. 2009, 24, 887-890.
Huang, et al. "Hispidulin, a constituent of Clerodendrum inerme that remitted motor tics, alleviated methamphetamine-induced hyperlocomotion without motor impairment in mice", J. Ethnopharmacol. 2015, 166, 18-22.
Liao, et al. "Hispidulin alleviated methamphetamine-induced hyperlocomotion by acting at alpha6 subunit-containing GABAA receptors in the cerebellum", Psychopharmacology 2016, 233, 3187-3199.
Kavvadias, et al, "The flavone hispidulin, a benzodiazepine receptor ligand with positive allosteric properties, traverses the blood-brain barrier and exhibits anticonvulsive effects", Br. J. Pharmacol. 2004, 142, 811-820.
Shi, et al. "Synthesis and biological evaluation of methylated scutellarein analogs based on metabolic mechanism of scutellarin in vivo", Eur. J. Med. Chem. 2015, 106, 95-105.
Lin, et al. "A new and practical synthetic method for the synthesis of 6-O-methyl-scutellarein: One metabolite of scutellarin in vivo", Int. J. Mol. Sci. 2015, 16, 7587-7594.
Chao, et al. "Total synthesis of hispidulin and the structural basis for its inhibition of proto-oncogene kinase Pim-1", J. Nat. Prod. 2015, 78, 1969-1976.
Shen, et al. "Efficient Synthesis of 6-O-methyl-scutellarein from Scutellarin via selective methylation", Lett. Org. Chem. 2013, 10, 733-737.
Zhang, et al. "A new and efficient synthesis of 6-O-methylscutellarein, the major metabolite of the natural medicine scutellarin", Molecules 2015, 20, 10184-10191.
Katsnelson, "Heavy drugs draw heavy interest from pharma backers", Nat. Med. 2013, 19, 656.
Gant, "Using deuterium in drug discovery: leaving the label in the drug", J. Med. Chem. 2014, 57, 3595-3611.
Tung, "Deuterium medicinal chemistry comes of age", Future Med. Chem. 2016, 8, 491-494.

*Primary Examiner* — Taofiq A Solola
(74) *Attorney, Agent, or Firm* — Amin, Turocy & Watson, LLP

(57) ABSTRACT

Provided is a method for preparing hispidulin or a derivative thereof. The method includes selective protection of trihydroxybenzaldehyde, followed by regioselective iodination, selective protection, Stille coupling, Baeyer-Villiger oxidation and basic hydrolysis to obtain a protected intermediate compound. Then, alkylation, Claisen-Schmidt condensation, cyclization and deprotection of the protected intermediate compound are performed to obtain hispidulin or the derivative thereof. The present disclosure provides an efficient method for total synthesis of hispidulin or the derivative thereof with concise reaction steps and high yield.

15 Claims, 4 Drawing Sheets

METHOD FOR PREPARING HISPIDULIN AND ITS DERIVATIVES

BACKGROUND

1. Technical Field

The present disclosure relates to a method for preparing hispidulin or a derivative thereof, and, for example, to a method for total synthesis of hispidulin and d-hispidulin (deuterium-labeled or d-labeled hispidulin).

2. Description of Associated Art

Hispidulin (6-methoxy-4',5,7-trihydroxyflavone) is a naturally occurring flavone belonging to a group of polyphenolic compounds named flavonoids, which occur ubiquitously in plants. Flavonoids are found to have many biological properties, such as antioxidative [1], anti-inflammatory [2], antimicrobial [3], anticonvulsant [4], antidepressant [5] and anticancer [6] activities.

Hispidulin is known to have various central nervous system activities. In particular, it was discovered as the main active ingredient from the leaf extract of *Clerodendrum inerme* (L.) Gaertn (Cl) [7] that significantly attenuated methamphetamine-induced hyperlocomotion (MIH) as a mouse model of motor tic, while not affecting the spontaneous locomotor activity or performance in mice even in amounts up to 100 mg/kg [8]. Further investigations showed that hispidulin formed strong bonds with $GABA_A$ receptors ($IC_{50}$=0.73 μM to 1.78 μM) and inhibited catecholamine-O-methyl-transferase (COMT) ($IC_{50}$=1.32 μM) [9]. By acting as a positive allosteric modulator (PAM), hispidulin enhanced cerebellar $α_6GABA_A$ receptor activity. It was noted that hispidulin had no hit on human ether-à-go-go-related gene (hERG) channels, an undesirable target in drug development [9], implying that hispidulin is a potential candidate for drug development.

Because of its interesting biological activity, there are several synthetic approaches developed to synthesize hispidulin [10-15]. For example, Shen and coworkers developed a strategy for semisynthesis of hispidulin in seven reaction steps by using a naturally occurring scutellarin (Scheme 1) [14]. Although this method is concise and has an overall yield as high as 10.7%, the researchers showed that, upon the large-scale synthesis of Formula 1, the protection of the catechol moiety of scutellarein using dichlorodiphenylmethane at 175° C. failed [12, 15]. While this problem was later solved through a seven-step synthesis route developed by Lin and coworkers, however the overall yield was reduced to 7.1% (Scheme 1) [12]. Zhang and coworkers then developed a scheme that only required four reaction steps (Scheme 1), but the nonselective methoxymethyl (MOM) protection of scutellarein caused the decrease in the overall yield of the synthesis of hispidulin (6.3%) [15]. Despite the satisfactory overall yield of these strategies, the tedious purification procedure required to isolate scutellarin from plants limits their use for large-scale preparation of hispidulin.

Scheme 1. Synthesis of hispidulin starting from scutellarin.

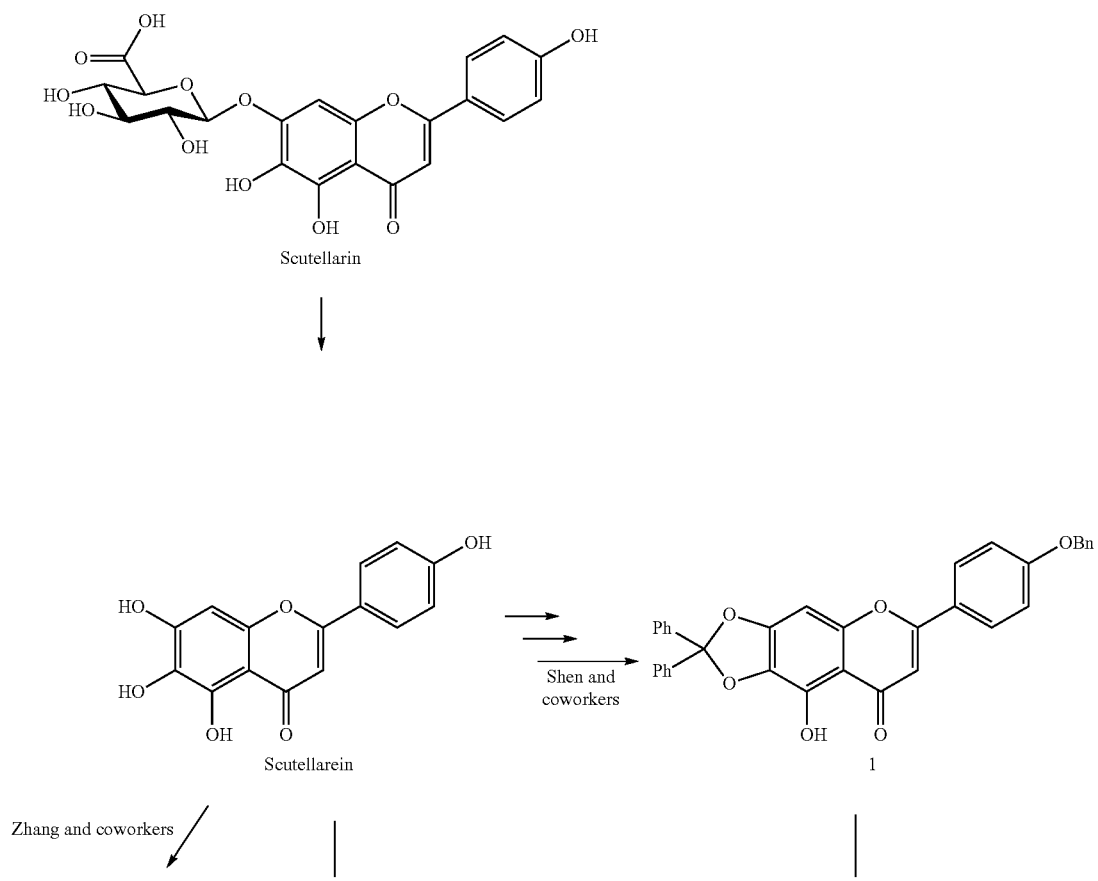

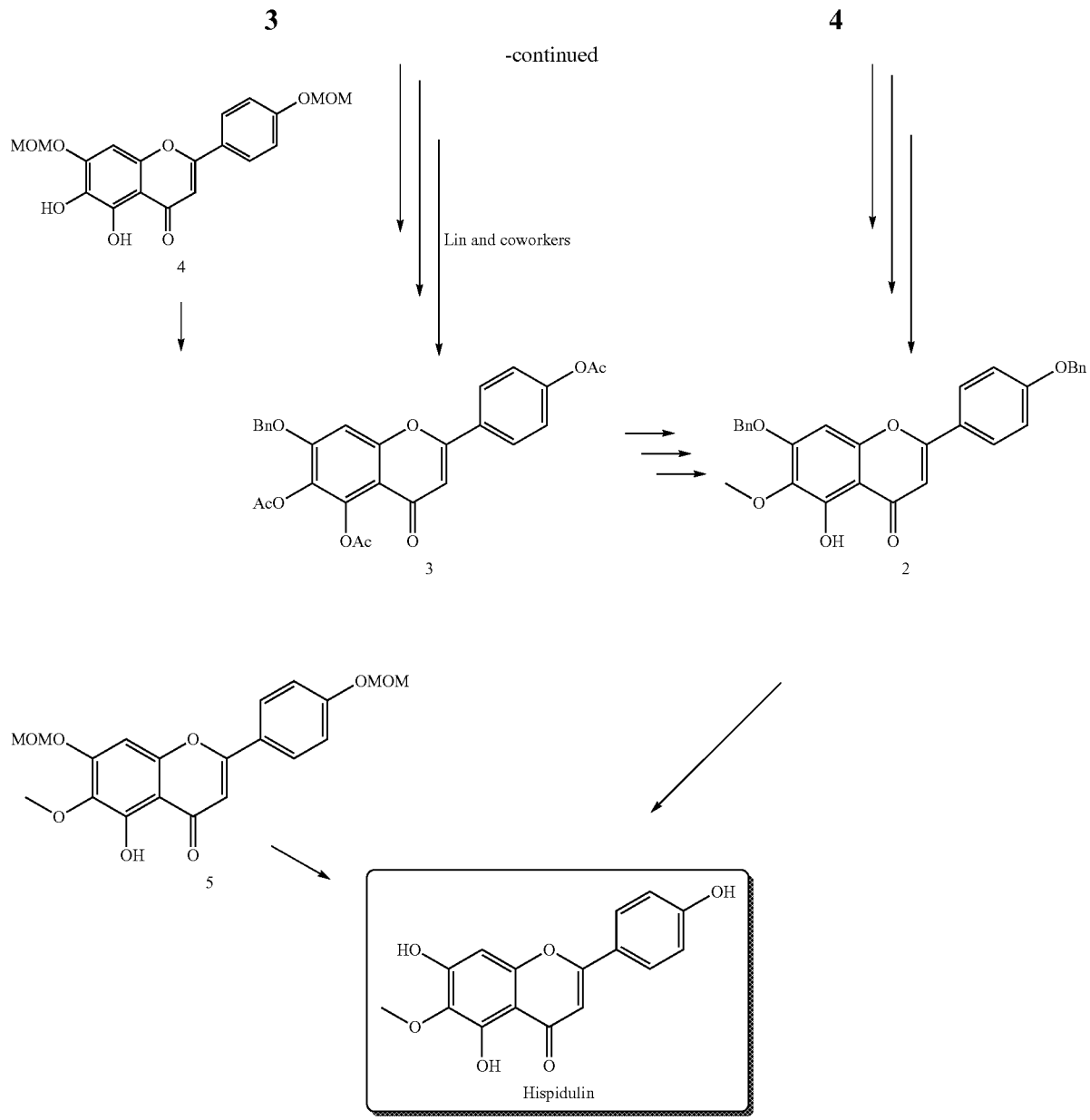

Kavvadias and coworkers developed a method synthesizing hispidulin from 2,4,6-trihydroxyacetophenone in nine reaction steps (Formula 6 in Scheme 2 below). However, the overall yield of this method is very limited (1.1%) [10].

Scheme 2. Synthesis of hispidulin by Kavvadias and coworkers.

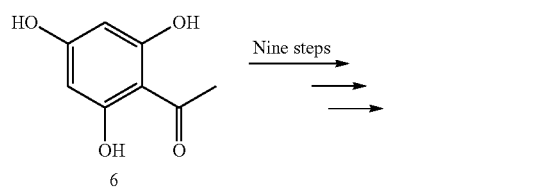

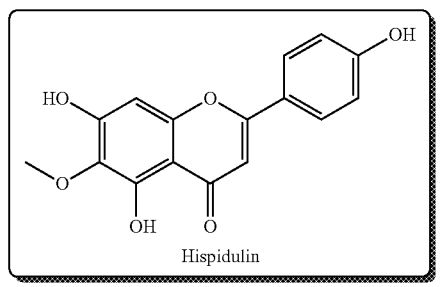

Scheme 3 below shows yet another approach aimed for a feasible and reproducible synthesis of hispidulin [13]. However, this method only slightly improved the overall yield due to the low yield of Friedel-Crafts acetylation of Formula 8 as well as unsatisfactory regioselective MOM protection of Formula 9.

Scheme 3. Synthesis of hispidulin by Chao et al.

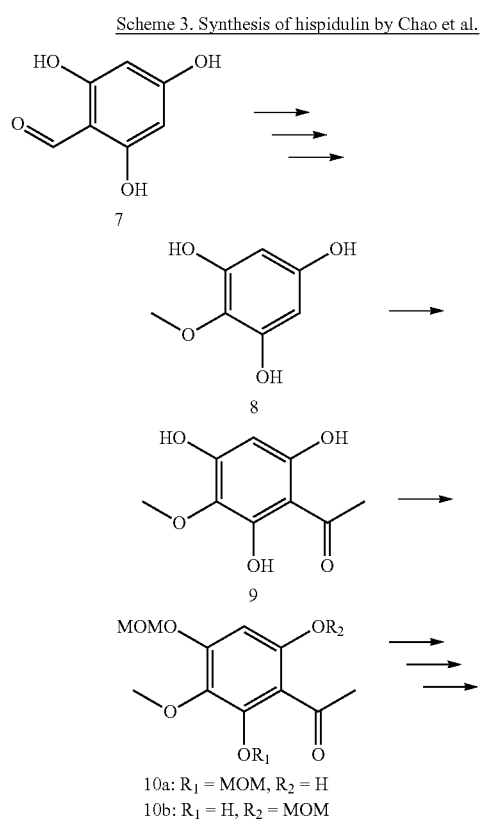

Accordingly, the previously proposed synthetic approaches to synthesize hispidulin have proven unsatisfactory due to their low feasibility and poor overall yields. There remains a need for an efficient and high-yield method to synthesize hispidulin.

SUMMARY

In view of the foregoing, the present disclosure provides an improved process for preparation of hispidulin or a derivative thereof. A unique and efficient strategy for synthesizing hispidulin or a derivative thereof is provided by the present disclosure.

In one embodiment, a new entity of hispidulin derivatives, i.e., a deuterium-labeled hispidulin, is also described in the present disclosure. In one embodiment, the deuterium-labeled hispidulin is of the formula

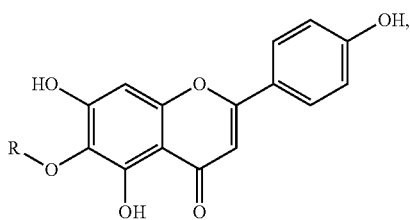

wherein R is $CD_3$.

Another embodiment of the present disclosure provides a method for preparing hispidulin or a derivative thereof from trihydroxybenzaldehyde, the method comprising providing an intermediate compound of following Formula (IV):

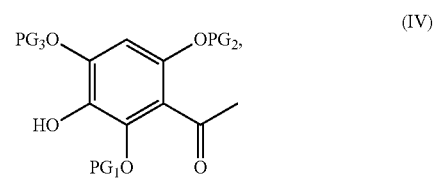

(IV)

wherein $PG_1$, $PG_2$ and $PG_3$ are each independently a hydroxyl protecting group.

In one embodiment, the hydroxyl protecting group is selected from the group consisting of methoxymethyl (MOM), 2-methoxyethoxymethyl (MEM), ethoxymethyl (EOM), t-butoxymethyl, benzyloxymethyl (BOM), p-methoxybenzyloxymethyl (PMBM), allyloxymethoxy, tetrahydropyranyl (THP), methylthiomethyl (MTM), tri-i-propylsilyloxymethyl (TOM), (phenyldimethylsilyl)methoxymethyl (SMOM), acetyl, pivaloyl (Piv), benzoate, methyl, ethyl, benzyl (Bn), p-methoxybenzyl (PMB), triphenylmethyl (Tr), methoxytrityl (MMT), dimethoxytrityl (DMT), trimethylsilyl (TMS), t-butyldimethylsilyl (TBDMS), triisopropylsilyl (TIPS), tri(trimethylsilyl)silyl (TTMSS), and t-butyldiphenylsilyl (TBDPS).

In another embodiment, the trihydroxybenzaldehyde is 2,4,6-trihydroxybenzaldehyde.

In yet another embodiment, the hispidulin or the derivative thereof prepared by the method of the present disclosure is of the formula

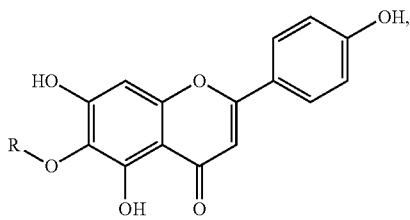

wherein R is hydrogen, an optionally substituted alkyl or an optionally substituted cycloalkyl. In an embodiment, the optionally substituted alkyl is $CH_3$, $C_2H_5$, or $C_3H_7$. In another embodiment, the optionally substituted cycloalkyl is $C_6H_5CH_2$.

In still yet another embodiment, the hispidulin derivative prepared by the method of the present disclosure is deuterium-labeled. In an embodiment, the deuterium-labeled hispidulin derivative has the formula

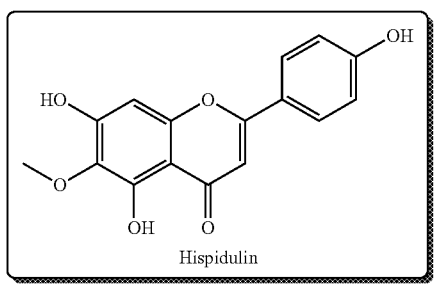

Hispidulin

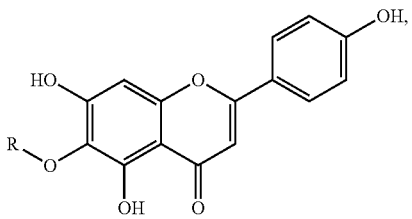

wherein R is CD$_3$.

In one embodiment, the intermediate compound of Formula (IV) is obtained by Baeyer-Villiger oxidation and basic hydrolysis of a compound represented by following Formula (V):

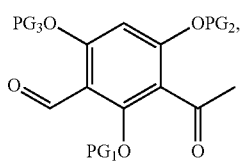

wherein PG$_1$, PG$_2$ and PG$_3$ are as defined above.

In one embodiment, Stille coupling is conducted to obtain the compound represented by Formula (V). In one embodiment, the Stille coupling is conducted with a palladium catalysts, such as Pd(PPh$_3$)$_4$, PdCl$_2$(PPh$_3$)$_2$, Pd(dppf)Cl$_2$, PdCl$_2$, Pd(OAc)$_2$, Pd(dba)$_2$, PdCl$_2$(MeCN)$_2$, BnPdCl(PPh$_3$)$_2$ and C$_4$H$_6$Br$_2$N$_2$Pd, coupled with an organic solvent, such as toluene, dioxane, tetrahydrofuran, acetonitrile, chloroform, dichloromethane, chlorobenzene, dimethylacetamide, methylpyrrolidone, dimethyl sulfoxide and hexamethylphosphoramide, or water. In a further embodiment, the Stille coupling is conducted with a yield of at least 60%, 70% or 80%. In still yet another embodiment, the Stille coupling is conducted with a reaction time of not more than 11 hours, 12 hours, 13 hours, 15 hours or 18 hours.

In another embodiment, the trihydroxybenzaldehyde reacts with at least one protecting group to obtain a compound represented by following Formula (VII)

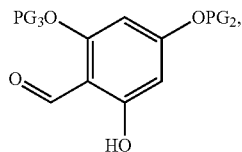

wherein PG$_2$ and PG$_3$ are as defined above, wherein the PG$_2$ and the PG$_3$ may be the same or different.

In yet another embodiment, the compound represented by Formula (VII) undergoes regioselective iodination and reacts with an additional protecting group to obtain a compound represented by following Formula (VI):

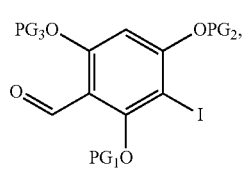

wherein PG$_1$, PG$_2$ and PG$_3$ are as defined above.

In one embodiment, the present disclosure provides a method for synthesizing the hispidulin or the derivative thereof with a yield of at least 12%, 15%, 18%, 20%, 25% or 26%.

In another embodiment, the compound represented by Formula (IV) undergoes alkylation and Claisen-Schmidt condensation, followed by deprotection to obtain a compound represented by following Formula (IA):

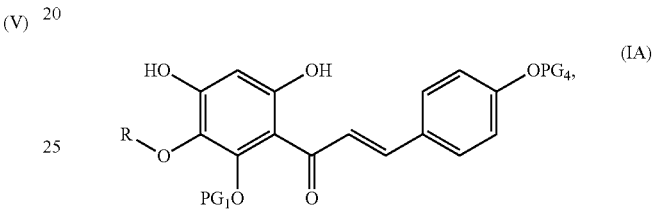

wherein PG$_1$ and PG$_4$ are each independently a hydroxyl protecting group as defined above, or PG$_4$ is independently H, and R is hydrogen, an optionally substituted alkyl or an optionally substituted cycloalkyl.

In a further embodiment, cyclization of the compound represented by Formula (IA) is conducted in the presence of a catalyst to obtain a compound represented by following Formula (IB):

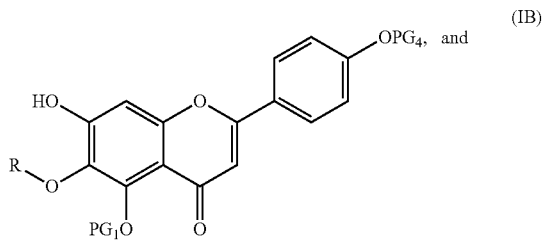

deprotection of the compound represented by Formula (IB) is conducted to obtain the hispidulin or the derivative thereof, wherein PG$_1$, PG$_4$ and R are as defined above. In yet another embodiment, the catalyst in the cyclization is catalytic I$_2$, potassium iodide, ammonium iodide, tetra-(n-butyl) ammonium iodide, selenium (IV) oxide, dihydrogen peroxide, cerium (IV) sulfate tetrahydrate, 2,3-dicyano-5,6-dichloro-p-benzoquinone or bis(acetoxy)iodobenzene. In another embodiment, the deprotection of the compound represented by Formula (IB) is debenzylation in a reaction with BCl$_3$, hydrogen, 10 wt. % palladium on activated carbon, titanium tetrachloride, boron tribromide, acetic acid or methanesulfonic acid. In still yet another embodiment, the deprotection of the compound represented by Formula (IB) is debenzylation in a reaction with BCl$_3$ at −80° C.

In one embodiment of the present disclosure, the method of synthesizing hispidulin or a derivative thereof comprises:

reacting 2,4,6-trihydroxybenzaldehyde with at least one protecting group to obtain a compound represented by following Formula (VII):

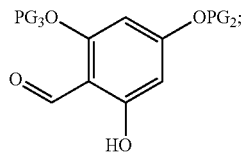

(VII)

conducting regioselective iodination of the compound represented by Formula (VII), and then reacting with an additional protecting group to obtain a compound represented by following Formula (VI):

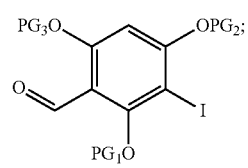

(VI)

conducting Stille coupling of the compound represented by Formula (VI) to obtain a compound represented by following Formula (V):

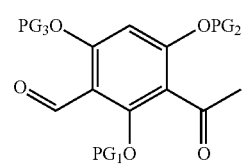

(V)

conducting Baeyer-Villiger oxidation and basic hydrolysis of the compound represented by Formula (V) to obtain an intermediate compound represented by Formula (IV):

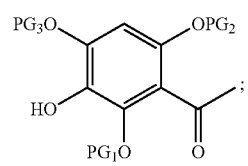

(IV)

alkylating the intermediate compound represented by Formula (IV) to obtain a compound represented by following Formula (IIA):

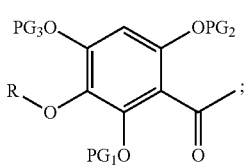

(IIA)

conducting Claisen-Schmidt condensation and deprotection of the compound represented by Formula (IIA) to obtain a compound represented by following Formula (IA):

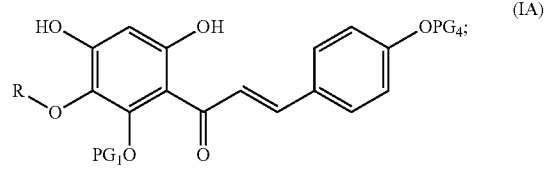

(IA)

conducting cyclization of the compound represented by Formula (IA) in the presence of a catalyst to obtain a compound represented by following Formula (IB):

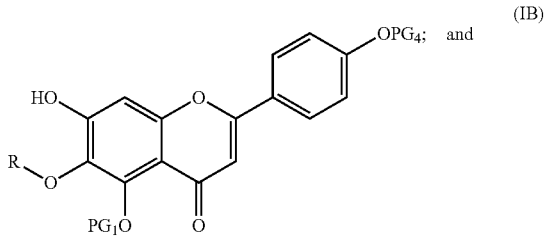

(IB)

deprotecting the compound represented by Formula (IB) to obtain the hispidulin or the derivative thereof, wherein $PG_1$, $PG_2$ and $PG_3$ each independently represent one of the following structures:

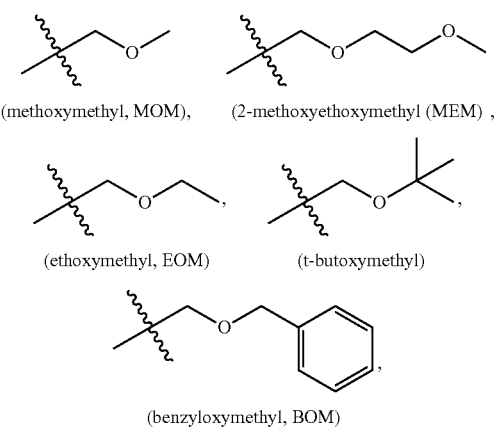

(methoxymethyl, MOM), (2-methoxyethoxymethyl (MEM), (ethoxymethyl, EOM) (t-butoxymethyl)

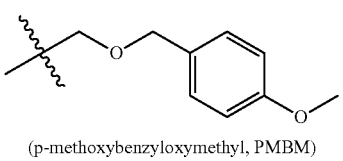

(benzyloxymethyl, BOM), (p-methoxybenzyloxymethyl, PMBM)

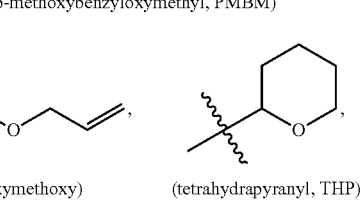

(allyloxymethoxy) (tetrahydropyranyl, THP)

-continued

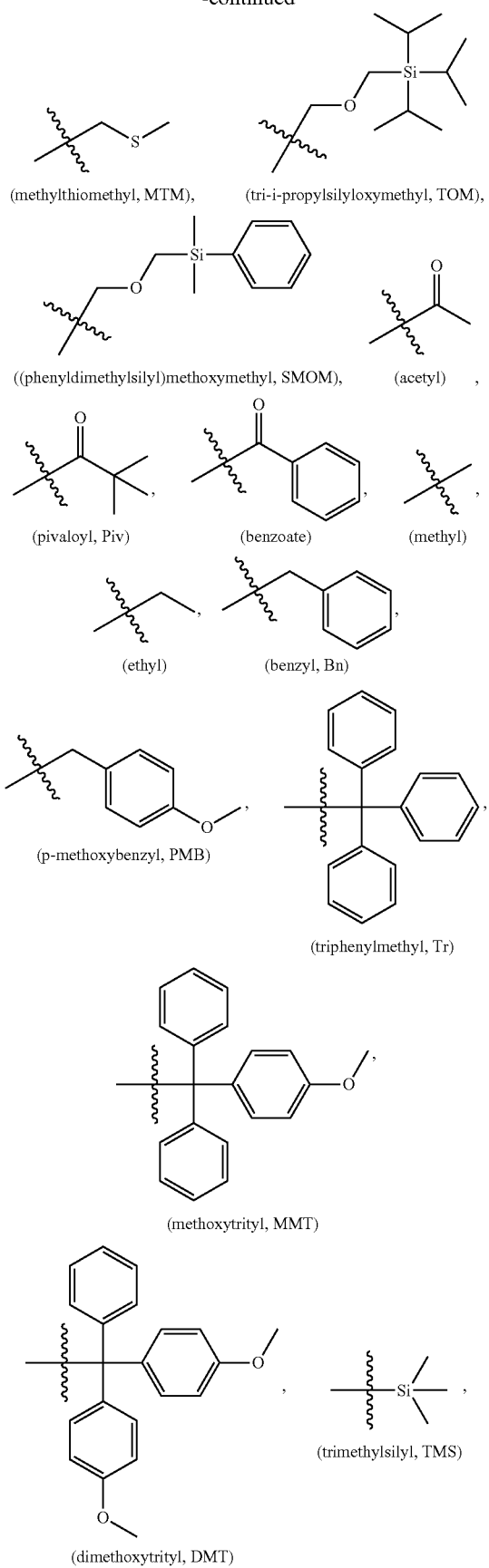

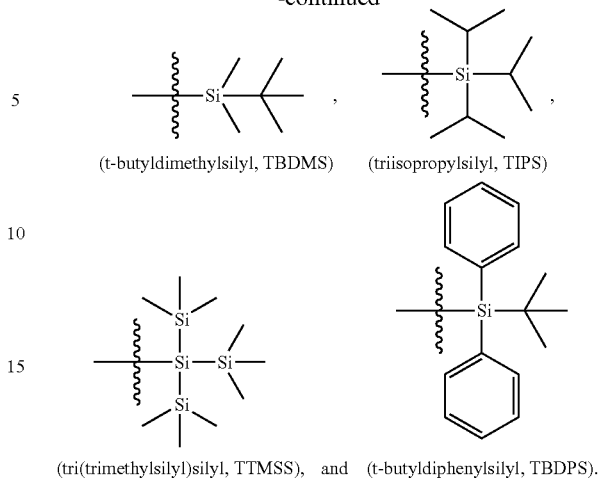

R is hydrogen, an optionally substituted alkyl or an optionally substituted cycloalkyl, and $PG_4$ is H or the same as defined in $PG_1$, $PG_2$ and $PG_3$.

DETAILED DESCRIPTION OF THE EMBODIMENTS

The following specific examples are used to exemplify the present disclosure. A person of ordinary skill in the art can conceive the other aspects of the present disclosure, based on the disclosure of the specification. The present disclosure can also be implemented or applied as described in different specific examples. It is possible to modify or alter the above examples for carrying out this disclosure without contravening its spirit and scope for different aspects and applications.

Strategies for synthesizing hispidulin can be classified as semisynthesis and total synthesis strategies. The starting material used in most semisynthetic methods is scutellarin, which is a natural product. Table 1 below shows that the semisynthesis routes had fewer reaction steps compared to the total synthesis methods; however, they need tedious isolation procedures for scutellarin, which limits the scale for further chemical modification. Furthermore, their overall yields are only 6.3% to 10.7%.

TABLE 1

Comparison of hispidulin synthesis methods.

| Synthesis Method by | Synthesis Route | Reaction Steps | Overall Yield (%) |
|---|---|---|---|
| Shen and coworkers | Semisynthesis | Seven | 10.7 |
| Lin and coworkers | Semisynthesis | Seven | 7.1 |
| Zhang and coworkers | Semisynthesis | Four | 6.3 |
| Kavvadias and coworkers | Total synthesis | Nine | 1.1 |
| Chao and coworkers | Total synthesis | Ten | 1.6 |
| This disclosure | Total synthesis | Eight | 26.9 |

For total synthesis, Kavvadias and coworkers developed a nine-step synthesis approach. The starting material used in this method is commercially available 2,4,6-trihydroxyacetophenone. Although this method solves the issue of the source for starting material, its drawback is a low overall yield [10]. Chao and coworkers also developed a feasible route of the hispidulin synthesis that has an overall yield comparable to that of the method developed by Kavvadias and coworkers [13]. The present disclosure provides a method for total synthesis of hispidulin with eight reaction steps. The present disclosure provides a synthesis method with more concise reaction steps, which has the highest overall yield of all currently known approaches to synthesize hispidulin.

Figure 1:
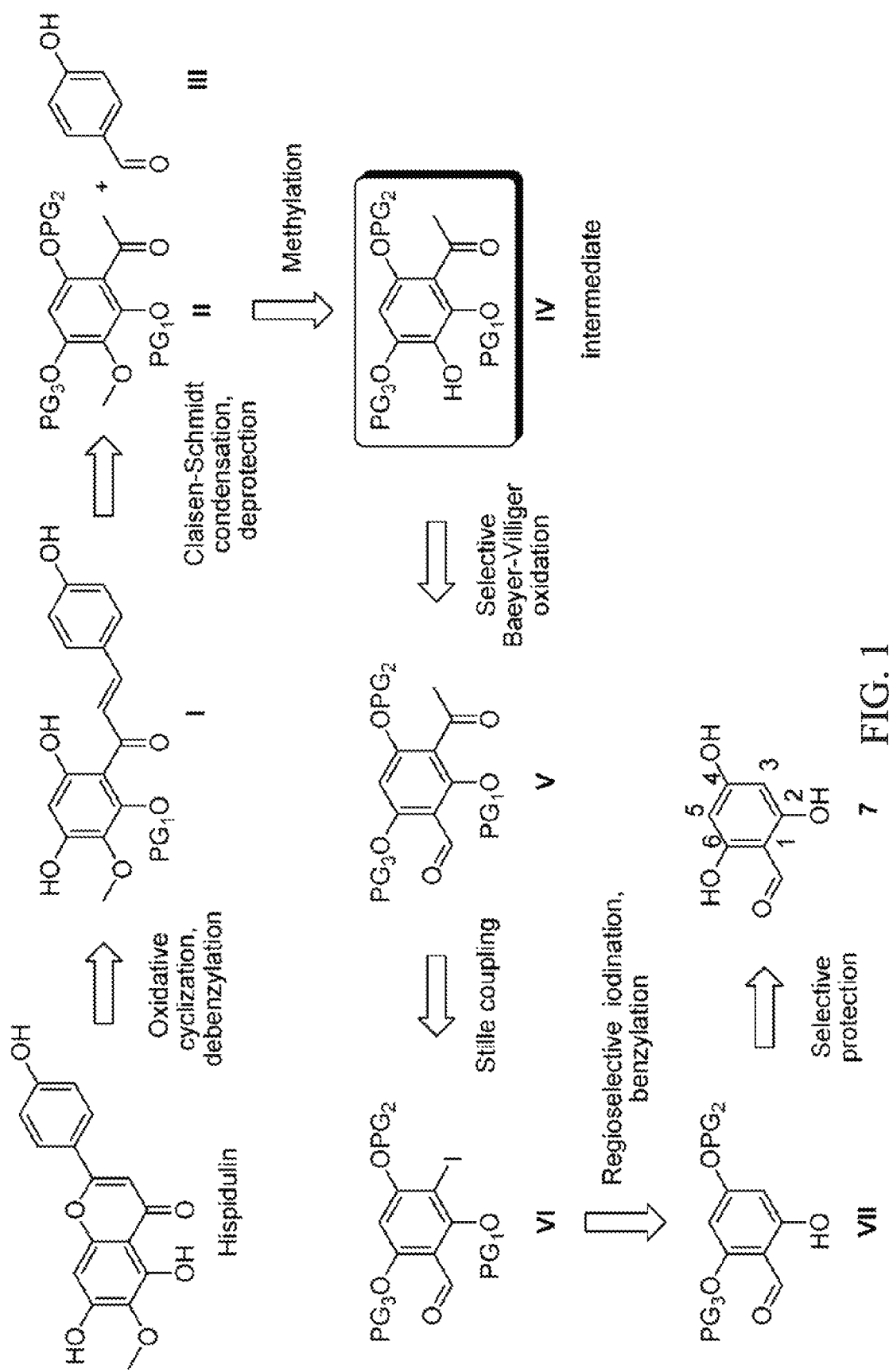
FIG. 1 shows the retrosynthetic analysis for hispidulin synthesis.

In the present disclosure, retrosynthetic analysis for synthesizing hispidulin is carried out and shown in FIG. 1. The retrosynthetic analysis showed that hispidulin can be produced from Formula (I) via debenzylation and oxidative cyclization. Formula (I) is derived from Formula (II) and commercially available Formula (III), which are used to conduct Claisen-Schmidt condensation and deprotection of protecting groups (PGs). Formula (II) in turn can be prepared from Formula (IV) via methylation. Formula (IV) is considered to be the intermediate that possesses the same or different protecting groups as well as acetyl and hydroxy moieties. Selective Bayer-Villiger reaction of Formula (V) provided Formula (IV). Formula (V) is prepared from Formula (VI) via Stille coupling. Substitution with the protecting groups and regioselective iodination of Formula (VII) gives Formula (VI). Starting from commercially available Formula 7, Formula (VII) is synthesized via selective protection.

Figure 2:
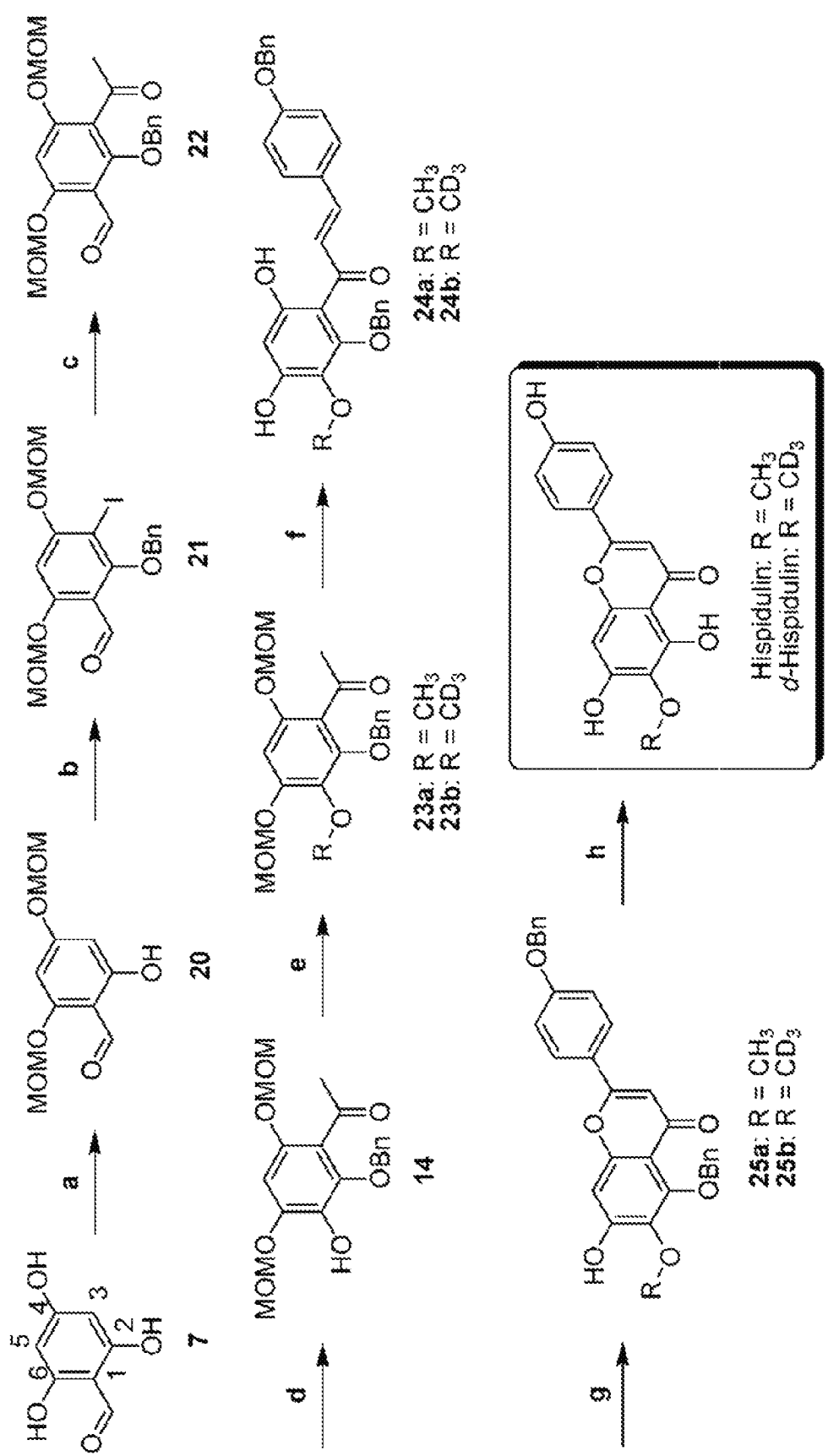
FIG. 2 shows the synthesis scheme for hispidulin and d-hispidulin. Reagents and conditions: (a) methoxymethyl chloride (MOMCl), N,N-diisopropylethylamine (DIPEA), $CH_2Cl_2$, 0° C., 80%; (b) (1) $CF_3COOAg$, $I_2$, $CH_2Cl_2$, 0° C.; (2) $K_2CO_3$, benzyl bromide (BnBr), dimethylformamide (DMF), 0° C., 89%; (c) tributyl(1-ethoxyvinyl)tin, $PdCl_2(PPh_3)_2$, toluene, 100° C., 83%; (d) (1) meta-chloroperoxybenzoic acid (MCPBA), $CH_2Cl_2$, 0° C.; (2) 10% $NaOH_{(aq)}$, MeOH, 68%; (e) 23a: $CH_3I$, $K_2CO_3$, acetone, 56° C., 92%; 23b: $CD_3I$, $K_2CO_3$, acetone, 56° C., 93%; (f) (1) BnOPhCHO, KOH, EtOH, $H_2O$, 0° C.; (2) c-HCl, MeOH, tetrahydrofuran (THF), 0° C.; 24a: 92%, 24b: 81%; (g) I2, dimethyl sulfoxide (DMSO), 120° C., 25a: 93%, 25b: 79%; (h) 1M BCl3 in hexane; CH2Cl2, −80° C., hispidulin: 85%, d-hispidulin: 80%.

Based on the retrosynthetic analysis, the present disclosure provides a novel synthesis method for hispidulin. In one embodiment of the present disclosure, as the scheme shown in FIG. 2, a method for preparation of hispidulin comprises reacting 2,4,6-trihydroxybenzaldehyde (Formula 7) with MOMCl to obtain the bis(methoxymethoxy)-protected compound represented by Formula 20; conducting regioselective iodination of the compound of Formula 20 and then reacting with BnBr to obtain the compound of Formula 21; conducting Stille coupling of the compound of Formula 21 to obtain the compound of Formula 22; conducting Baeyer-Villiger oxidation and basic hydrolysis of the compound of Formula 22 to obtain the compound of Formula 14; methylating the compound of Formula 14 by using $CH_3I$ or $CD_3I$ to obtain the compound of Formula 23 (wherein the compound of Formula 23a contains R as being $CH_3$, and the compound of Formula 23b contains R as being $CD_3$); conducting Claisen-Schmidt condensation of Formula 23 by 4-(benzyloxy) benzaldehyde prior to MOM deprotection to obtain chalcone represented by Formula 24 (wherein chalcone represented by Formula 24a contains R as being $CH_3$, and chalcone represented by Formula 24b contains R as being $CD_3$); cyclizing chalcone represented by Formula 24 in the presence of catalytic $I_2$ to obtain flavone represented by Formula 25 (wherein flavone represented by Formula 25a contains R as being $CH_3$, and flavone represented by Formula 25b contains R as being $CD_3$); conducting debenzylation of flavone represented by Formula 25 in a reaction using $BCl_3$ at −80° C. to obtain hispidulin or d-hispidulin.

The present disclosure further provides a synthesis method for deuterium-labeled (d-labeled) hispidulin. Deuterium is a stable isotope of hydrogen. Because deuterium has a stronger chemical bond with carbon than hydrogen, deuterium-labeled compounds can affect the absorption, distribution, metabolism and toxicology of their counterpart compounds [16, 17].

In the present disclosure, $C_6$—$OCH_3$ in hispidulin is replaced with $C_6$—$OCD_3$. The synthesis of d-hispidulin according to the present disclosure is described in FIG. 2, wherein Formula 14 is methylated by using $CD_3I$ to obtain Formula 23b; Claisen-Schmidt condensation of Formula 23b is conducted with 4-(benzyloxy)benzaldehyde prior to MOM deprotection to obtain chalcone 24b; chalcone 24b is cyclized in the presence of catalytic $I_2$ to obtain flavone 25b; and debenzylation of flavone 25b is conducted in a reaction using $BCl_3$ at −80° C. to obtain d-hispidulin.

The present disclosure therefore also provides a new hispidulin derivative entity, i.e., a deuterium-labeled (d-labeled) hispidulin.

As used herein, the terms "hydrogen or hydroxyl protecting group" refer to protecting groups that protect hydrogen or hydroxy groups. It is to be understood that such protecting groups are conventional and routinely selected to allow a synthetic or chemical transformation to be performed in a manner that the hydroxy group does not interfere with or is not changed by the synthetic or chemical transformation performed. Illustrative, but not exclusive, examples of such protecting groups may be found in Greene & Wuts "Protective Groups in Organic Synthesis," 2nd Ed., John Wiley & Sons, New York, 1991; the disclosure of which is incorporated herein by reference. Further illustrative of such protecting groups are those particularly suitable for protecting phenols and catechols, and the analogs and derivatives thereof.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$ alkyl, $C_1$-$C_4$ alkyl, methyl, ethyl, propyl, 3-methylpentyl, and the like.

As used herein "cycloalkyl" is intended to indicate a saturated cycloalkane hydrocarbon radical, comprising 3-6 carbon atoms, e.g., cyclopropyl, cyclobutyl, cyclopentyl and cyclohexyl.

The new hispidulin synthesis method disclosed in the present disclosure is more feasible compared to all methods previously reported. In particular, the present disclosure has the highest overall yield, and synthesizes $C_6$—$OCH_3$-containing hispidulin derivatives efficiently. The synthesis method disclosed in the present disclosure can also be used to synthesize d-labeled hispidulin. The present disclosure also provides a method to produce 6-OMe-containing hispidulin derivatives as new chemical entities.

The following are specific examples further demonstrating the implementation of the current disclosure, but not to limit the scope of the current disclosure.

EXAMPLES

General materials and methods used in the following examples are described herein. The NMR spectra ($^1$H- and $^{13}$C-NMR, ROESY, HSQC and HMBC) were obtained with a Bruker AV500 using standard pulse programs. The MS data were recorded with a Finnigan Mat TSQ-7000 mass spectrometer (HR-ESI-MS) (Thermo, Ringoes, N.J., USA). The HPLC was performed on a Cis column (150 mm×4.6 mm, Ascentis) by using an L-2130 pump (Hitachi, Ibaraki, Japan) and a UV/vis L-2420 detector (Hitachi, Ibaraki, Japan). The column chromatography was performed on silica gel (70-230 mesh, Merck, Darmstadt, Germany). All TLC analyses were performed on silica gel plates (KG60-F254, Merck, Darmstadt, Germany). Reagents and materials were used without further purification, and chemicals were purchased from ACROS (Geel, Belgium). Dry dichloromethane was distilled from $CaH_2$ under nitrogen atmosphere. MOMCl was acquired from TCI (Tokyo, Japan), and 2,4,6-trihydroxybenzaldehyde was purchased from Alfa Aesar (Heydham, UK).

Example 1: Preparation of 2-Hydroxy-4,6-bis(methoxymethoxy)benzaldehyde (Formula 20)

To a solution of Formula 7 (10 g, 64.9 mmol) in $CH_2Cl_2$ (200 mL) was added DIPEA (28.3 mL, 162.2 mmol). The resulting mixture was stirred for 10 min in an ice-bath under $N_2$. MOMCl (10.8 mL, 142.7 mmol) was added dropwise to the reaction mixture by an addition funnel. The reaction mixture was warmed to room temperature (rt) and stirred for 3 h. The mixture was concentrated in vacuo. The residue was diluted with EtOAc (100 mL) and washed with distilled $H_2O$ (3×80 mL). The organic layer was dried over $Na_2SO_4$, filtered and removed in vacuo. The residue was purified by silica gel chromatography (EtOAc:n-hexane=1:9) to obtain Formula 20 (12.3 g, 80%), light-yellow microcrystalline powder; $^1$H-NMR ($CDCl_3$, 300 MHz) δ 12.29 (1H, s), 10.16 (1H, s), 6.25 (1H, d, J=2.1 Hz), 6.23 (1H, d, J=2.1 Hz), 5.24 (2H, s), 5.18 (2H, s), 3.51 (3H, s), 3.47 (3H, s); $^{13}$C-NMR ($CDCl_3$, 125 MHz) δ 192.1, 165.6, 165.5, 161.2, 106.9, 96.6, 94.6, 94.1, 94.0, 56.6, 56.5; HR-ESI-MS m/z 243.0858+ (calcd. for $C_{11}H_{15}O_6$, 243.0863).

Example 2: Preparation of 2-Benzyloxy-3-iodo-4,6-bis(methoxymethoxy)benzaldehyde (Formula 21)

Figure 3:
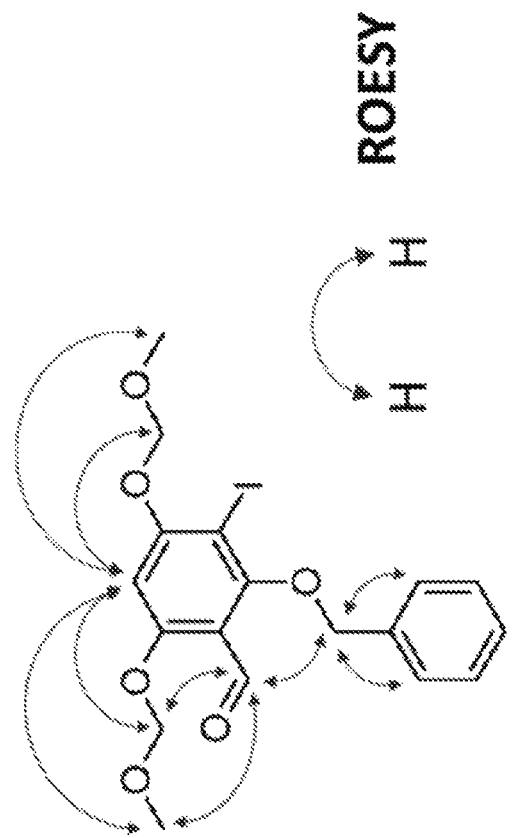
FIG. 3 shows the rotating frame nuclear Overhauser effect spectroscopy (ROESY) correlations of Formula 21.
Figure 3:
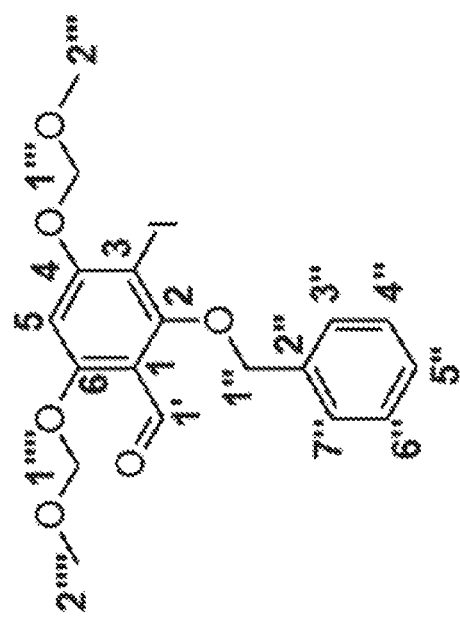

To a mixture of Formula 20 (7.2 g, 29.6 mmol) and $CF_3CO_2Ag$ (7.8 g, 35.5 mmol) in $CH_2Cl_2$ (150 mL) at 0° C. was added $I_2$ (8.3 g, 32.5 mmol) in $CH_2Cl_2$ (200 mL) dropwise by an addition funnel over 2 h. The reaction mixture was warmed to rt and stirred for 3 h. Then, saturated $Na_2S_2O_{3(aq)}$ (50 mL) was added, and the mixture was washed with distilled $H_2O$ (3×100 mL). The organic layer was dried over $Na_2SO_4$, filtered and removed in vacuo. The residue was dissolved in DMF (100 mL), and then $K_2CO_3$ (7.2 g, 51.8 mmol) was added. Benzyl bromide (460 µL, 3.9 mmol) was added dropwise to the mixture by an addition funnel at 0° C. The resulting solution was warmed to rt and stirred for 3 h. The mixture was diluted with EtOAc (300 mL) and washed with distilled $H_2O$ (3×100 mL). The organic layer was dried over $Na_2SO_4$, filtered and removed in vacuo. The residue was purified by silica gel chromatography (EtOAc:n-hexane=1:5) to obtain Formula 21 (12.1 g, 89%), white microcrystalline powder; $^1$H-NMR ($CDCl_3$, 300 MHz) δ 10.30 (1H, s), 7.66 (2H, dd, J=1.8, 8.1 Hz), 7.45-7.36 (3H, m), 6.84 (1H, s), 5.32 (2H, s), 5.29 (2H, s), 4.99 (2H, s), 3.54 (3H, s), 3.52 (3H, s); $^{13}$C-NMR ($CDCl_3$, 125 MHz) δ 187.2, 161.9, 161.8, 161.6, 136.1, 129.0, 128.5, 128.4, 115.5, 98.2, 95.2, 94.9, 78.5, 56.7; HR-ESI-MS m/z 459.0294 [M+H]$^+$ (calcd. for $C_{18}H_{20}O_6I$, 459.0299). The chemical structure of Formula 21 was confirmed by rotating frame nuclear Overhauser effect spectroscopy (ROESY) spectrum. FIG. 3 shows the correlation of H-5 (δH 6.84) to H-2''' (δH 3.52), H-2'''' (δH 3.54), H-1''' (δH 5.29) and H-1'''' (δH 5.32); and H-1' (δH 10.30) to H-2'''' (δH 3.54), H-1'' (δH 4.99) and H-1'''' (δH 5.32).

Example 3: Preparation of 3-Acetyl-2-benzyloxy-4,6-bis(methoxymethoxy) benzaldehyde (Formula 22)

Table 2 below shows how tributyl(1-ethoxyvinyl)tin was used to optimize Stille coupling.

TABLE 2

Optimization of reaction condition for Stille coupling of Formula 21.

| Entry | Catalyst | Solvent | Yield (%) | Reaction Time (h) |
|---|---|---|---|---|
| 1 | Pd(PPh$_3$)$_4$ | Dioxane | 68 | 30 |
| 2 | Pd(PPh$_3$)$_4$ | Toluene | 70 | 24 |
| 3 | PdCl$_2$(PPh$_3$)$_2$ | Dioxane | 73 | 20 |
| 4 | PdCl$_2$(PPh$_3$)$_2$ | Toluene | 83 | 10 |
| 5 | Pd(dppf)Cl$_2$ | Dioxane | 34 | 78 |
| 6 | Pd(dppf)Cl$_2$ | Toluene | 53 | 43 |

First, catalyst Pd(PPh$_3$)$_4$ was used in dioxane at 100° C. The reaction had a satisfactory yield (68%), but the reaction time was up to 30 h. Replacement of the solvent by toluene led to the decrease of the reaction time to 24 h. Further experiments using palladium catalysts such as PdCl$_2$(PPh$_3$)$_2$ and Pd(dppf)Cl$_2$ in dioxane or toluene showed that PdCl$_2$(PPh$_3$)$_2$ significantly improved the yield and decreased the reaction time. For example, PdCl$_2$(PPh$_3$)$_2$ coupled with toluene not only gave the highest yield, but also had the lowest reaction time.

To a mixture of Formula 21 (5 g, 10.9 mmol) and PdCl$_2$(PPh$_3$)$_2$ (766 mg, 1.1 mmol) in toluene (200 mL) was added tributyl(1-ethoxyvinyl)tin (5.5 mL, 16.4 mmol). The resulting solution was heated to 100° C. and stirred for 12 h. After cooling to rt, the reaction mixture was acidified with 1 M HCl (50 mL) and stirred for 30 min. The mixture was diluted with EtOAc (200 mL) and washed with distilled $H_2O$ (3×100 mL). The organic layer was dried over $Na_2SO_4$, filtered and concentrated in vacuo. The residue was purified by silica gel chromatography (EtOAc:n-hexane=1:4) to obtain Formula 22 (3.5 g, 83%), yellow microcrystalline powder; $^1$H-NMR ($CDCl_3$, 300 MHz) δ 10.37 (1H, s), 7.48 (2H, dd, J=1.8, 7.8 Hz), 7.41-7.33 (3H, m), 6.80 (1H, s), 5.29 (2H, s), 5.24 (2H, s), 4.96 (2H, s), 3.53 (3H, s), 3.49 (3H, s), 2.43 (3H, s); $^{13}$C-NMR ($CDCl_3$, 125 MHz) δ 200.9, 187.3, 162.1, 159.3, 158.4, 136.1, 129.0, 128.8, 128.6, 128.5, 128.4, 121.8, 114.3, 97.5, 95.0, 94.5, 79.1, 56.8, 32.5; HR-ESI-MS m/z 375.1432+(calcd. for $C_{20}H_{23}O_7$, 375.1438).

Example 4: Preparation of 2-Benzyloxy-3-hydroxy-4,6-bis(methoxymethoxy) acetophenone (Formula 14)

To a solution of 70% MCPBA (6.8 g, 27.6 mmol) in dry $CH_2Cl_2$ (100 mL) at 0° C. was added Formula 22 (3.4 g, 9.2 mmol) in CH$_2$Cl$_2$ (100 mL) dropwise by an addition funnel over 1 h. The resulting solution was warmed to rt and stirred for 8 h. Then, saturated Na$_2$S$_2$O$_{3(aq)}$ (30 mL) was added, and the reaction mixture was washed with distilled H$_2$O (3×100 mL). The organic layer was dried over Na$_2$SO$_4$, filtered and concentrated in vacuo. The residue was dissolved in MeOH (80 mL) and 10% NaOH$_{(aq)}$ (60 mL) was added. The resulting solution was stirred at rt for 1.5 h. The mixture was diluted with EtOAc (250 mL) and washed with distilled H$_2$O (3×100 mL). The organic layer was dried over Na$_2$SO$_4$, filtered and concentrated in vacuo. The residue was purified by silica gel chromatography (EtOAc:n-hexane=1:4) to obtain Formula 14 (2.3 g, 68%), light-yellow oil; $^1$H-NMR (CDCl$_3$, 300 MHz) δ 7.44 (2H, dd, J=1.8, 8.1 Hz), 7.40-7.32 (3H, m), 6.76 (1H, s), 5.61 (1H, s), 5.21 (2H, s), 5.08, (2H, s), 5.06 (2H, s), 3.53 (3H, s), 3.46 (3H, s), 2.45 (3H, s); $^{13}$C-NMR (CDCl$_3$, 125 MHz) δ 201.3, 146.6, 146.2, 143.2, 136.9, 134.9, 128.5, 128.3, 122.1, 100.4, 96.0, 95.8, 76.3, 56.6, 56.3, 32.6; HR-ESI-MS m/z 363.1431 [M+H]$^+$ (calcd. for C$_{19}$H$_{23}$O$_7$, 363.1438).

Example 5: Preparation of 2-Benzyloxy-3-methoxy-4,6-bis(methoxymethoxy) acetophenone (Formula 23a)

To a mixture of Formula 14 (587 mg, 1.6 mmol) and K$_2$CO$_3$ (1.1 g, 8.1 mmol) in acetone (20 mL) was added CH$_3$I (0.5 mL, 8.1 mmol). The resulting solution was heated to 56° C. and stirred for 5 h. The reaction mixture was concentrated in vacuo, diluted with EtOAc (100 mL) and washed with distilled H$_2$O (3×50 mL). The organic layer was dried over Na$_2$SO$_4$, filtered and concentrated in vacuo. The residue was purified by silica gel chromatography (EtOAc:n-hexane=1:5) to obtain Formula 23a (558 mg, 92%), white microcrystalline powder; $^1$H-NMR (CDCl$_3$, 300 MHz) δ 7.42 (2H, dd, J=2.0, 8.3 Hz), 7.40-7.32 (3H, m), 6.76 (1H, s), 5.23 (2H, s), 5.11 (2H, s), 5.07 (2H, s), 3.85 (3H, s), 3.53 (3H, s), 3.46 (3H, s), 2.38 (3H, s); $^{13}$C-NMR (CDCl$_3$, 125 MHz) δ 200.6, 151.8, 149.4, 149.2, 137.9, 136.7, 128.1, 128.0, 127.7, 121.4, 99.6, 95.0, 94.9, 76.0, 60.8, 56.0, 55.9, 32.1; HR-ESI-MS m/z 377.1587 [M+H]$^+$ (calcd. for C$_{20}$H$_{25}$O$_7$, 377.1595).

Example 6: Preparation of 2-Benzyloxy-3-[2H3]-methoxy-4,6-bis(methoxymethoxy) acetophenone (Formula 23b)

Following the procedure as described for Formula 23a, the reaction of Formula 14 (1.8 g, 4.8 mmol), K$_2$CO$_3$ (3.3 g, 24.2 mmol), and CD$_3$I (1.5 mL, 24.2 mmol) in acetone (40 mL) gave Formula 23b (1.7 g, 93%), white microcrystalline powder; $^1$H-NMR (CDCl$_3$, 300 MHz) δ 7.42 (2H, dd, J=2.1, 8.4 Hz), 7.39-7.31 (3H, m), 6.76 (1H, s), 5.23 (2H, s), 5.11 (2H, s), 5.07 (2H, s), 3.53 (3H, s), 3.46 (3H, s), 2.38 (3H, s); $^{13}$C-NMR (CDCl$_3$, 125 MHz) δ 200.6, 151.8, 149.4, 149.2, 137.8, 136.7, 128.1, 128.0, 127.7, 121.4, 99.6, 95.0, 94.9, 76.0, 56.0, 55.9, 32.1; HR-ESI-MS m/z 380.1775 [M+H]$^+$ (calcd. for C$_{20}$H$_{22}$D$_3$O$_7$, 380.1783).

Example 7: Preparation of (E)-1-(2-Benzyloxy-4,6-dihydroxy-3-methoxyphenyl)-3-(4-benzyloxyphenyl)prop-2-en-1-one (Formula 24a)

To a solution of Formula 23a (545 mg, 1.45 mmol) and 4-benzyloxybenzaldyde (615 mg, 2.9 mmol) in EtOH (20 mL) was added KOH (813 mg, 14.5 mmol) in EtOH—H$_2$O (3 mL:3 mL) dropwise by an addition funnel at 0° C. over 30 min. The resulting solution was warmed to rt and stirred for 24 h. The mixture was diluted with distilled H$_2$O (50 mL) and washed with EtOAc (3×50 mL). The organic layer was dried over Na$_2$SO$_4$, filtered and concentrated in vacuo. MeOH-THF (14.5 mL:14.5 mL) and 12 M HCl (0.7 mL) were added to the residue at 0° C. The resulting solution was warmed to rt and stirred for 8 h. The reaction mixture was diluted with distilled H$_2$O (50 mL) and washed with EtOAc (3×50 mL). The organic layer was dried over Na$_2$SO$_4$, filtered and concentrated in vacuo. The residue was purified by silica gel chromatography (EtOAc:n-hexane=1:4) to obtain Formula 24a (641 mg, 92%), microcrystalline powder; $^1$H-NMR (DMSO-d$_6$, 300 MHz) δ 12.92 (1H, s), 10.52 (1H, s), 7.59 (2H, s), 7.48-7.45 (2H, m), 7.44-7.37 (5H, m), 7.32-7.29 (5H, m), 6.94 (2H, d, J=8.8 Hz), 6.21 (1H, s), 5.16 (2H, s), 5.06 (2H, s), 3.77 (3H, s); $^{13}$C-NMR (DMSO-d$_6$, 125 MHz) δ 192.0, 160.2, 159.6, 157.7, 153.1, 143.0, 136.7, 136.6, 134.4, 130.3, 128.5, 128.4, 128.3, 128.2, 128.0, 127.8, 127.4, 124.6, 115.2, 109.0, 99.7, 75.7, 69.4, 60.7; HR-ESI-MS m/z 483.1795+(calcd. for C$_{30}$H$_{27}$O$_6$, 483.1802).

Example 8: Preparation of (E)-1-(2-Benzyloxy-4,6-dihydroxy-3-[2H3]methoxyphenyl)-3-(4-benzyloxyphenyl)prop-2-en-1-one (Formula 24b)

According to the procedure as described for Formula 24a, reaction of Formula 23b (1.0 g, 2.6 mmol), 4-benzyloxybenzaldyde (1.1 g, 5.3 mmol) and KOH (1.5 g, 26.4 mmol) in EtOH (60 mL) followed by treatment of 12 M HCl (1.3 mL) and MeOH-THF (26.4 mL:26.4 mL) gave Formula 24b (1.0 g, 81%), yellow microcrystalline powder; $^1$H-NMR (DMSO-d$_6$, 300 MHz) δ 12.95 (1H, s), 10.54 (1H, s), 7.59 (2H, s), 7.48-7.45 (2H, m), 7.44-7.36 (5H, m), 7.33-7.29 (5H, m), 6.94 (2H, d, J=8.8 Hz), 6.22 (1H, s), 5.16 (2H, s), 5.06 (2H, s); $^{13}$C-NMR (DMSO-d$_6$, 125 MHz) δ 192.0, 160.2, 159.7, 157.7, 153.2, 143.0, 136.7, 136.6, 134.4, 130.3, 128.5, 128.4, 128.3, 128.2, 128.0, 127.8, 127.4, 124.6, 115.2, 109.0, 99.7, 75.7, 69.4; HR-ESI-MS m/z 486.1983 [M+H]$^+$ (calcd. for C$_{30}$H$_{24}$D$_3$O$_6$, 486.1990).

Example 9: Preparation of 4'-Benzyloxy-6-methoxy-5-benzyloxy-7-hydroxyflavone (Formula 25a)

To a solution of Formula 24a (598 mg, 1.2 mmol) in dry DMSO (100 mL) was added I$_2$ (32 mg, 0.1 mmol) in DMSO (3 mL) dropwise by syringe. The resulting solution was heated to 120° C., and stirred for 2 h. After cooling to rt, saturated Na$_2$S$_2$O$_{3(aq)}$ (10 mL) was added to the reaction mixture. The mixture was diluted with EtOAc (100 mL) and washed with distilled H$_2$O (3×50 mL). The organic layer was dried over Na$_2$SO$_4$, filtered and concentrated in vacuo. The residue was purified by silica gel chromatography (EtOAc:n-hexane=1:3) to obtain Formula 25a (555 mg, 93%), yellow microcrystalline powder; $^1$H-NMR (DMSO-d$_6$, 300 MHz) δ 10.76 (1H, s), 7.98 (2H, d, J=8.9 Hz), 7.61 (2H, d, J=7.0 Hz), 7.48 (2H, d, J=7.0 Hz), 7.44-7.34 (6H, m), 7.18 (2H, d, J=8.9 Hz), 6.91 (1H, s), 6.67 (1H, s), 5.22 (2H, s), 5.00 (2H, s), 3.75 (3H, s); $^{13}$C-NMR (DMSO-d$_6$, 125 MHz) δ 175.8, 160.9, 160.1, 156.1, 153.8, 150.7, 139.6, 137.6, 136.6, 128.5, 128.3, 128.1, 128.0, 127.8, 123.4, 115.3, 111.4, 106.0, 100.1, 75.6, 69.5, 60.9; HR-ESI-MS m/z 481.1637 [M+H]$^+$ (calcd. for C$_{30}$H$_{25}$O$_6$, 481.1646).

Example 10: Preparation of 4'-Benzyloxy-6-methoxy-5-benzyloxy-7-hydroxyflavone (Formula 25b)

Following the procedure as described for Formula 25a, reaction of Formula 24b (849 mg, 1.7 mmol) with I$_2$ (44 mg, 0.2 mmol) in DMSO (120 mL) gave Formula 25b (664 mg, 79%), yellow microcrystalline powder; $^1$H-NMR (DMSO-$d_6$, 300 MHz) δ 10.75 (1H, s), 7.98 (2H, d, J=8.9 Hz), 7.61 (2H, d, J=6.8 Hz), 7.48 (2H, dd, J=1.8, 8.4 Hz), 7.44-7.34 (6H, m), 7.18 (2H, d, J=8.9 Hz), 6.91 (1H, s), 6.67 (1H, s), 5.22 (2H, s), 5.01 (2H, s); $^{13}$C-NMR (DMSO-$d_6$, 125 MHz) δ 175.8, 160.9, 160.1, 156.1, 153.7, 150.7, 139.5, 137.6, 136.6, 128.5, 128.3, 128.1, 128.0, 127.8, 123.4, 115.3, 111.4, 106.0, 100.1, 75.6, 69.5; HR-ESI-MS m/z 484.1827 [M+H]$^+$ (calcd. for $C_{30}H_{22}D_3O_6$, 484.1834).

Example 11: Preparation of Hispidulin

Figure 4:
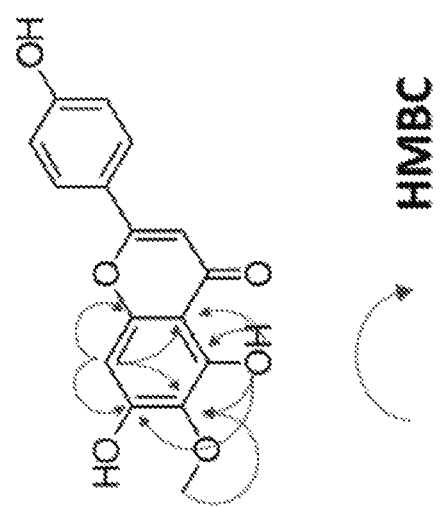
FIG. 4 shows the ROESY correlations and heteronuclear multiple bond correlations (HMBCs) of hispidulin.
Figure 4:
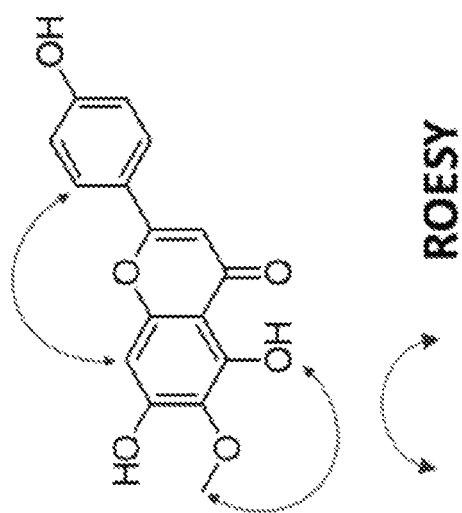
Figure 4:
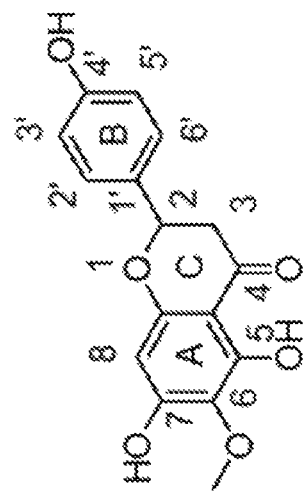

To a solution of Formula 25a (301 mg, 0.6 mmol) in dry $CH_2Cl_2$ (40 mL) was added 1 M $BCl_3$ (2.5 mL, 2.5 mmol) in dry $CH_2Cl_2$ (5 mL) dropwise by syringe at −78° C. over 20 min. The resulting solution was stirred for 1 h. The reaction mixture was diluted with distilled $H_2O$ (50 mL) and washed with EtOAc (3×50 mL). The organic layer was dried over $Na_2SO_4$, filtered and concentrated in vacuo. The residue was purified by silica gel chromatography (EtOAc:n-hexane=1:2) to obtain hispidulin (160 mg, 85%), yellow microcrystalline powder; $^1$H-NMR (DMSO-$d_6$, 500 MHz) δ 13.07 (1H, s, 5-OH), 10.73 (1H, s, 7-OH), 10.38 (1H, s, 4'-OH), 7.92 (2H, d, J=8.9 Hz, H-2', H-6'), 6.92 (2H, d, J=8.9 Hz, H-3', H-5'), 6.77 (1H, s, H-3), 6.59 (1H, s, H-8), 3.74 (3H, s, 6-OMe); $^{13}$C-NMR (DMSO-$d_6$, 125 MHz) δ 182.2 (C-4), 163.9 (C-2), 161.2 (C-4'), 157.3 (C-7), 152.8 (C-5), 152.4 (C-9), 131.4 (C-6), 128.5 (C-2', C-6'), 121.2 (C-1'), 116.0 (C-3', C-5'), 104.1 (C-10), 102.4 (C-3), 94.3 (C-8), 60.0 (6-OMe); HR-ESI-MS m/z 301.0702 [M+H]$^+$ (calcd. for $C_{16}H_{13}O_6$, 301.0707). The chemical structure of hispidulin was identified by 2D-NMR analyses. FIG. 4 shows the correlation in the ROESY spectrum of hispidulin that 5-OH (δH 13.07) was correlated to 6-OMe''' (δH 3.74) and H-8 (δH 6.59) was correlated to H-2' and H-6' (δH 7.92). Additionally, the HMBC spectrum showed that 5-OH (δH 13.07) correlated to C-5 (δC 152.8), C-6 (δC 131.4), C-7 (δC 157.3), C-9 (δC 152.4) and C-10 (δC 104.1); H-8 (δH 13.07) correlated to C-6 (δC 131.4), C-7 (δC 157.3), C-9 (δC 152.4) and C-10 (δC 104.1); and 6-OMe-H (δH 3.74) correlated to C-6 (δC 131.4). The $^1$H- and $^{13}$C-NMR data of synthesized hispidulin were similar to those of hispidulin previously isolated.

Example 12: Preparation of d-Hispidulin

Following the procedure as described for hispidulin, reaction of Formula 25b (536 mg, 1.1 mmol) in $CH_2Cl_2$ (75 mL) with 1 M $BCl_3$ (4.4 mL, 4.4 mmol) in $CH_2Cl_2$ (8.8 mL) gave d-hispidulin (268 mg, 80%), yellow microcrystalline powder; $^1$H-NMR (DMSO-$d_6$, 500 MHz) δ 13.07 (1H, s, 5-OH), 10.70 (1H, s, 7-OH), 10.36 (1H, s, 4'-OH), 7.91 (2H, d, J=8.9 Hz, H-2', H-6'), 6.92 (2H, d, J=8.9 Hz, H-3', H-5'), 6.76 (1H, s, H-3), 6.58 (1H, s, H-8); $^{13}$C-NMR (DMSO-$d_6$, 125 MHz) δ 182.1 (C-4), 163.8 (C-2), 161.2 (C-4'), 157.2 (C-7), 152.8 (C-5), 152.4 (C-9), 131.3 (C-6), 128.5 (C-2', C-6'), 121.2 (C-1'), 116.0 (C-3', C-5'), 104.1 (C-10), 102.4 (C-3), 94.2 (C-8); HR-ESI-MS m/z 304.0888 [M+H]$^+$ (calcd. for $C_{16}H_{10}D_3O_6$, 304.0895).

Due to the absence of a proton signal of the $CD_3O$ group in the $^1$H-NMR spectra of the d-containing intermediate compounds 23b, 24b, 25b and d-hispidulin, these compound structures were identified depending on the $^{13}$C-NMR spectra without $^1$H decoupling and the mass technique. The $^{13}$C-NMR spectra revealed a characteristic multiplet splitting pattern of the $^{13}$C signal for the $CD_3O$ group in compounds 23b, 24b, 25b and d-hispidulin. The mass spectra also supported chemical structures of these d-labeled compounds. All synthesized compounds had an estimated purity of at least 98% as determined by HPLC analysis Example 13: Human Liver Microsome Stability Metabolic stability is associated with susceptibility of compounds to biotransformation. Metabolic half-life ($t_{1/2}$) and intrinsic clearance ($CL_{int}$) were compared between hispidulin and d-hispidulin by testing these synthesized compounds in a human liver microsome stability assay.

Mixed-gender human liver microsomes (Lot #1210347) were purchased from XenoTech. The reaction mixture minus NADPH was prepared as described below. The test compounds were added into the reaction mixture at a final concentration of 1 μM. A separate reaction with the control compound, testosterone, was conducted simultaneously with the reactions with the test compounds. An aliquot of the reaction mixture (without cofactor) was equilibrated in a shaking water bath at 37° C. for 3 min After addition of cofactor to initiate the reaction, the mixture was incubated in a shaking water bath at 37° C. Aliquots (100 μL) were withdrawn at 0, 10, 20, 30 and 60 min for the test compounds and testosterone. The reaction was terminated by immediately combining the tested compounds and testosterone samples with 400 μL of ice-cold 50/50 acetonitrile (ACN)/$H_2O$ containing 0.1% formic acid and internal standard. The samples were then mixed and centrifuged to precipitate proteins. All samples were assayed by LC-MS/MS using electrospray ionization. The peak area response ratio (PARR) to internal standard was compared to the PARR at time 0 to determine the percent remaining at each time point. The values for half-life ($t_{1/2}$) and intrinsic clearance ($CL_{int}$) of the tested compounds were determined by Absorption System Corp. Half-life calculated using GraphPad software was fitted to a single-phase exponential decay equation.

The FDA-approved deuterated agent, deutetrabenazine, had a $t_{1/2}$ (8.6 h) superior to tetrabenazine (4.8 h). In addition to $t_{1/2}$, the area under the curve (AUC) of deutetrabenazine (542 ng·hr/mg) was also higher than that of its counterpart compound (261 ng·hr/mg) [18]. In the present disclosure, hispidulin and d-hispidulin had no significant difference in $t_{1/2}$ and $CL_{int}$ (Table 3), which suggested that the C6-OMe of hispidulin is resistant to be modified by the human liver microsome.

TABLE 3

Human liver microsome stability of hispidulin and d-hispidulin.

| Compound | Half-Life (min) | $CL_{int}$[1] (mL/min/mg Protein) |
|---|---|---|
| Hispidulin | 46 | 0.0298 |
| d-Hispidulin | 43 | 0.0325 |
| Testosterone | 19 | 0.0727 |

[1]Intrinsic clearance ($CL_{int}$) was calculated based on $CL_{int}$ = k/P, where k is the elimination rate constant and P is the protein concentration in the incubation.

The references listed below cited in the application are each incorporated by reference as if they were incorporated individually.

REFERENCES

1. Pietta, P. G. Flavonoids as antioxidants. *J. Nat. Prod.* 2000, 63, 1035-1042.

2. Serafini, M.; Peluso, I.; Raguzzini, A. Flavonoids as anti-inflammatory agents. *Proc. Nutr. Soc.* 2010, 69, 273-278.
3. Cushnie, T. P.; Lamb, A. J. Antimicrobial activity of flavonoids. *Int. J. Antimicrob. Agents* 2005, 26, 343-356.
4. Cardenas-Rodriguez, N.; Gonzalez-Trujano, M. E.; Aguirre-Hernandez, E.; Ruiz-Garcia, M.; Sampieri, A., III; Coballase-Urrutia, E.; Carmona-Aparicio, L. Anticonvulsant and antioxidant effects of *Tilia americana* var. *mexicana* and flavonoids constituents in the pentylenetetrazole-induced seizures. *Oxid. Med. Cell. Longev.* 2014, 2014, 329172.
5. Guan, L. P.; Liu, B. Y. Antidepressant-like effects and mechanisms of flavonoids and related analogues. *Eur. J. Med. Chem.* 2016, 121, 47-57.
6. Ravishankar, D.; Rajora, A. K.; Greco, F.; Osborn, H. M. Flavonoids as prospective compounds for anti-cancer therapy. *Int. J. Biochem. Cell Biol.* 2013, 45, 2821-2831.
7. Fan, P. C.; Huang, W. J.; Chiou, L. C. Intractable chronic motor tics dramatically respond to *Clerodendrum inerme* (L) Gaertn. *J. Child Neurol.* 2009, 24, 887-890.
8. Huang, W. J.; Lee, H. J.; Chen, H. L.; Fan, P. C.; Ku, Y. L.; Chiou, L. C. Hispidulin, a constituent of *Clerodendrum inerme* that remitted motor tics, alleviated methamphetamine-induced hyperlocomotion without motor impairment in mice. *J. Ethnopharmacol.* 2015, 166, 18-22.
9. Liao, Y. H.; Lee, H. J.; Huang, W. J.; Fan, P. C.; Chiou, L. C. Hispidulin alleviated methamphetamine-induced hyperlocomotion by acting at alpha6 subunit-containing GABAA receptors in the cerebellum. *Psychopharmacology* 2016, 233, 3187-3199.
10. Kavvadias, D.; Sand, P.; Youdim, K. A.; Qaiser, M. Z.; Rice-Evans, C.; Baur, R.; Sigel, E.; Rausch, W. D.; Riederer, P.; Schreier, P. The flavone hispidulin, a benzodiazepine receptor ligand with positive allosteric properties, traverses the blood-brain barrier and exhibits anticonvulsive effects. *Br. J. Pharmacol.* 2004, 142, 811-820.
11. Shi, Z. H.; Li, N. G.; Wang, Z. J.; Tang, Y. P.; Dong, Z. X.; Zhang, W.; Zhang, P. X.; Gu, T.; Wu, W. Y.; Yang, J. P. et. al. Synthesis and biological evaluation of methylated scutellarein analogs based on metabolic mechanism of scutellarin in vivo. *Eur. J. Med. Chem.* 2015, 106, 95-105.
12. Lin, H.; Zhang, W.; Dong, Z. X.; Gu, T.; Li, N. G.; Shi, Z. H.; Kai, J.; Qu, C.; Shang, G. X.; Tang, Y. P. et. al. A new and practical synthetic method for the synthesis of 6-O-methyl-scutellarein: One metabolite of scutellarin in vivo. *Int. J. Mol. Sci.* 2015, 16, 7587-7594.
13. Chao, S. W.; Su, M. Y.; Chiou, L. C.; Chen, L. C.; Chang, C. I.; Huang, W. J. Total synthesis of hispidulin and the structural basis for its inhibition of proto-oncogene kinase Pim-1. *J. Nat. Prod.* 2015, 78, 1969-1976.
14. Shen, M. Z.; Shi, Z. H.; Li, N. G.; Tang, H.; Shi, Q. P.; Tang, Y. P.; Yang, J. P.; Duan, J. A. Efficient Synthesis of 6-O-methyl-scutellarein from Scutellarin via selective methylation. *Lett. Org. Chem.* 2013, 10, 733-737.
15. Zhang, W.; Dong, Z. X.; Gu, T.; Li, N. G.; Zhang, P. X.; Wu, W. Y.; Yu, S. P.; Tang, Y. P.; Yang, J. P.; Shi, Z. H. A new and efficient synthesis of 6-O-methylscutellarein, the major metabolite of the natural medicine scutellarin. *Molecules* 2015, 20, 10184-10191.
16. Katsnelson, A. Heavy drugs draw heavy interest from pharma backers. *Nat. Med.* 2013, 19, 656.
17. Gant, T. G. Using deuterium in drug discovery: leaving the label in the drug. *J. Med. Chem.* 2014, 57, 3595-3611.
18. Tung, R. D. Deuterium medicinal chemistry comes of age. *Future Med. Chem.* 2016, 8, 491-494.

What is claimed is:
1. A method for preparing hispidulin or a derivative thereof from trihydroxybenzaldehyde, the method comprising:
providing an intermediate compound represented by following Formula (IV):

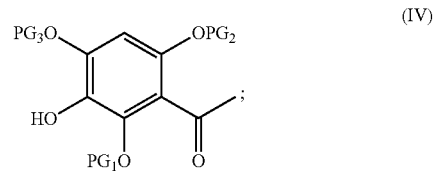

performing alkylation and Claisen-Schmidt condensation of the intermediate compound, followed by deprotection to obtain a compound represented by following Formula (IA):

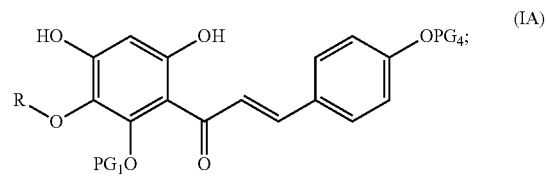

performing cyclization of the compound represented by Formula (IA) in the presence of a catalyst to obtain a compound represented by following Formula (IB):

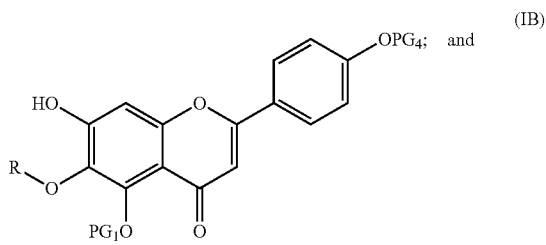

deprotecting the compound represented by Formula (IB) to obtain the hispidulin or the derivative thereof having following formula:

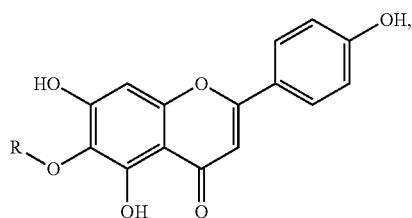

wherein $PG_1$, $PG_2$, $PG_3$ and $PG_4$ are each independently a hydroxyl protecting group selected from the group consisting of methoxymethyl (MOM), 2-methoxyethoxymethyl (MEM), ethoxymethyl (EOM), t-butoxymethyl, benzyloxymethyl (BOM), p-methoxybenzyloxymethyl (PMBM), allyloxymethoxy, tetrahydropyranyl (THP), methylthiomethyl (MTM), tri-i-propylsilyloxymethyl (TOM), (phenyldimethylsilyl)methoxymethyl (SMOM), acetyl, pivaloyl (Piv), benzoate, methyl, ethyl, benzyl (Bn), p-methoxybenzyl (PMB), triphenylmethyl (Tr), methoxytrityl (MMT), dimethoxytrityl (DMT), trimethylsilyl (TMS), t-butyldimethylsilyl (TBDMS), triisopropylsilyl (TIPS), tri(trimethylsilyl)silyl (TTMSS), and t-butyldiphenylsilyl (TBDPS), and R is hydrogen, an optionally substituted alkyl or an optionally substituted cycloalkyl.

2. The method of claim 1, wherein the trihydroxybenzaldehyde is 2,4,6-trihydroxybenzaldehyde.

3. The method of claim 1, wherein the optionally substituted alkyl is selected from the group consisting of $CH_3$, $C_2H_5$, and $C_3H_7$.

4. The method of claim 1, wherein the optionally substituted cycloalkyl is $C_6H_5CH_2$.

5. The method of claim 1, wherein the hispidulin derivative is deuterium-labeled.

6. The method of claim 5, wherein the deuterium-labeled hispidulin derivative has following formula:

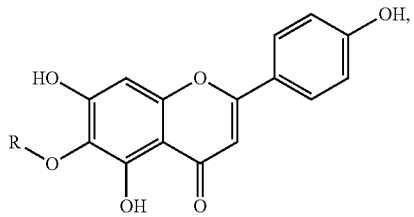

wherein R is $CD_3$.

7. The method of claim 1, wherein the intermediate compound is obtained by Baeyer-Villiger oxidation and basic hydrolysis of a compound represented by following Formula (V):

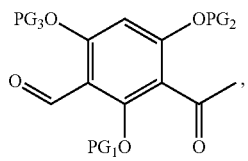

wherein $PG_1$, $PG_2$ and $PG_3$ are as defined in claim 1.

8. The method of claim 1, wherein the trihydroxybenzaldehyde reacts with at least one protecting group to obtain a compound represented by following Formula (VII):

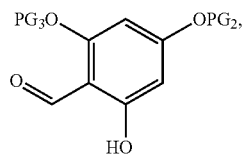

wherein $PG_2$ and $PG_3$ are as defined in claim 1.

9. The method of claim 8, wherein the compound represented by Formula (VII) undergoes regioselective iodination and reacts with an additional protecting group to obtain a compound represented by following Formula (VI):

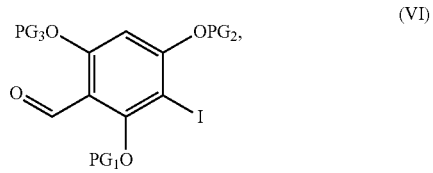

wherein $PG_1$, $PG_2$ and $PG_3$ are as defined in claim 1.

10. The method of claim 9, further comprising conducting Stille coupling to obtain the compound represented by following Formula (V):

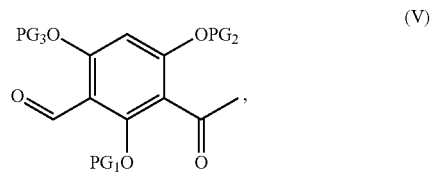

wherein $PG_1$, $PG_2$ and $PG_3$ are as defined in claim 1.

11. The method of claim 10, wherein the Stille coupling is conducted with a palladium catalyst and an organic solvent.

12. The method of claim 11, wherein the palladium catalyst is $Pd(PPh_3)_4$, $PdCl_2(PPh_3)_2$, $Pd(dppf)Cl_2$, $PdCl_2$, $Pd(OAc)_2$, $Pd(dba)_2$, $PdCl_2(MeCN)_2$, $BnPdCl(PPh_3)_2$, or $C_4H_6Br_2N_2Pd$.

13. The method of claim 11, wherein the organic solvent is toluene, dioxane, tetrahydrofuran, acetonitrile, chloroform, dichloromethane, chlorobenzene, dimethylacetamide, methylpyrrolidone, dimethyl sulfoxide, or hexamethylphosphoramide.

14. The method of claim 1, wherein the catalyst in the cyclization is catalytic 12, potassium iodide, ammonium iodide, tetra-(n-butyl)ammonium iodide, selenium (IV) oxide, dihydrogen peroxide, cerium (IV) sulfate tetrahydrate, 2,3-dicyano-5,6-dichloro-p-benzoquinone or bis(acetoxy)iodobenzene.

15. The method of claim 1, wherein the deprotecting is debenzylation of the compound represented by Formula (IB) in a reaction with $BCl_3$, hydrogen, palladium on activated carbon, titanium tetrachloride, boron tribromide, acetic acid or methanesulfonic acid.

* * * * *